United States Patent
Komachiya et al.

(10) Patent No.: US 6,592,732 B1
(45) Date of Patent: Jul. 15, 2003

(54) GAS COMPONENTS MEASURING DEVICE

(75) Inventors: Masahiro Komachiya, Hitachinaka (JP); Seikou Suzuki, Hitachiohta (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/485,228
(22) PCT Filed: Mar. 23, 1999
(86) PCT No.: PCT/JP99/01440
§ 371 (c)(1),
(2), (4) Date: Feb. 7, 2001
(87) PCT Pub. No.: WO00/57167
PCT Pub. Date: Sep. 28, 2000

(51) Int. Cl.[7] .............................................. G01N 27/407
(52) U.S. Cl. ........................ 204/426; 204/425; 204/408; 205/781
(58) Field of Search .......................... 204/408, 421–429

(56) References Cited

U.S. PATENT DOCUMENTS

| | | | |
|---|---|---|---|
| 4,298,573 A | * | 11/1981 | Fujishiro |
| 4,300,991 A | * | 11/1981 | Chiba et al. |
| 4,487,680 A | * | 12/1984 | Logothetis et al. |
| 4,810,350 A | * | 3/1989 | Mantese et al. |
| 4,861,456 A | * | 8/1989 | Mase et al. |
| 5,186,809 A | * | 2/1993 | Aoyama et al. |
| 5,242,573 A | * | 9/1993 | Hayakawa et al. |
| 5,474,665 A | * | 12/1995 | Friese et al. |
| 5,851,376 A | * | 12/1998 | Nishioka et al. |
| 6,077,409 A | * | 6/2000 | Lee et al. |
| 6,224,727 B1 | * | 5/2001 | Miyata et al. |

* cited by examiner

Primary Examiner—T. Tung
(74) Attorney, Agent, or Firm—Crowell & Moring LLP (57) ABSTRACT

In a maltilayer exhaust gas component sensor for measuring $NO_x$ (nitrogen oxide) and HC (hydrocarbon), the reliability and the productivity are improved without degrading the detecting sensitivity.

A gas sensing portion is formed by laminating porous solid electrolyte layers having gas permeability together with an electrode protecting film, porous electrodes having catalytic activity, a porous electric insulating layer and a closely-compacted (dense) solid electrolyte layer, and by placing a heater as a temperature control means in contact with or near the laminated layer body.

12 Claims, 9 Drawing Sheets

GAS COMPONENTS MEASURING DEVICE

FIELD OF THE INVENTION

The present invention relates to a sensor for measuring exhaust gas components such as nitrogen oxides and hydrocarbons produced in a combustion process and a sensing technology using the sensor. Further, the present invention relates to exhaust gas component measurement in industrial fields requiring combustion control such as a waste incinerating facility and, more particularly to a system technology for measuring an exhaust gas concentration under a high temperature atmosphere such as a vehicle and controlling combustion state based on the measured result.

BACKGROUND OF THE INVENTION

There area various kinds of exhaust gas component sensors. The exhaust gas components here mean gas components other than the main components of atmosphere of nitrogen and oxygen, and gas components contained in trace amounts in an exhaust gas. The exhaust gas component sensor means a sensor for the measurement of the exhaust gases. Typical sensors can be roughly classified into semiconductor sensors and solid electrolyte sensors. The semiconductor sensor utilizes the phenomenon that concentration of conductive carriers changes when a gas to be measured is chemically adsorbed to a semiconductor element (sensing element). The change in concentration of a measured gas can be measured by converting to change in electric resistance of the semiconductor element. Nitrogen oxide ($NO_X$) sensors used for the deoxidizing denitration process of an incinerator have been studied, and the operating temperature is in a medium-low temperature range of 200 to 400° C. On the other hand, the solid electrolyte sensor can stably operate at a temperature above 500 to 600° C. Therefore, the solid electrolyte sensor becomes a focus of attention as a gas sensor usable under a high temperature exhaust gas atmosphere, for example, usable for a vehicle.

An oxygen sensor using zirconia partially stabilized by adding yttria (YSZ) as a solid electrolyte is already used as a vehicle mounted sensor, and an exhaust gas sensor similarly using the YSZ as a main component is proposed. An $NO_X$ sensor is described in detail in Japanese Patent Application Laid-Open No.10-142194, and a hydrocarbon (HC) sensor is described in Japanese Patent Application Laid-Open No.10-19843. Structure of the sensing portion of these exhaust gas component sensors is formed by performing necessary shaping of a green sheet of the solid electrolyte, laminating the shaped green sheets together with platinum electrodes, and then baking the laminated structure. Since the sensor has the structure of laminating a plurality of layers including structures of a measurement chamber and a gas passage together with the electrodes, the sensor can be called as a multilayer sensor.

On the other hand, in regard to the multilayer exhaust gas component sensor, an example of employing a porous solid electrolyte layer having gas permeability is disclosed in Japanese Patent Application Laid-Open No.7-260741. In this exhaust gas component sensor, the measurement chamber and the gas passage are eliminated, and the sensor is formed by using one porous solid electrolyte layer. In order to improve sensing accuracy, a protective layer having a gas selectivity is provided in addition to general electrode protective layers.

Both of the multilayer exhaust gas component sensors described in Japanese Patent Application Laid-Open No.10- 142194 and in Japanese Patent Application Laid-Open No.10-19843 are suitable for a small sized and high performance sensor. However, they have a problem in that cracks are apt to occur at baking or during being used under a heating condition. It was found by classifying fracture modes that the cracks were produced more often by other causes different from the inter-layer separation or delamination. Occurrence of the cracks needs some starting points. The starting point may be a portion where different materials are in contact with each other or a portion where thermal and/or intrinsic stress is concentrated. In the case of the multilayer sensor, a gap portion of the measurement chamber provided inside the layer or a boundary between different materials is apt to become the starting point. Therefore, in order to suppress occurrence of the cracks in the conventional sensor having the above-mentioned structure, careful attentions on homogeneity of the materials and on temperature control and so on are required at manufacturing the sensors. In addition to this, the multilayer exhaust gas component sensor has a problem in that there is limitation in simplification of the manufacturing process because it has various kinds of structures inside one layer. In more detail, in the conventional structure, the whole laminated body is difficult to be formed through a printing method because the gap portion needs to be formed in the structure.

Further, although the multilayer exhaust gas component sensor disclosed in Japanese Patent Application Laid-Open No.7-260741 is simple in structure and little in occurrence of the cracks, it has a problem in that sufficient sensing accuracy can not be obtained. An amount of the exhaust gas components is very small compared to an amount of nitrogen and oxygen. Taking an example of the $NO_X$ concentration in a vehicle exhaust gas, the $NO_X$ concentration is 0.05% or less compared to 20% of the concentration of oxygen which can be an interference gas. In order to improve the sensing accuracy, it is necessary to remove oxygen which exists in bulk and has an ill effect on measurement, and then sensing the very small amount of the exhaust gas. In the multilayer exhaust gas component sensor formed by using one porous solid electrolyte layer disclosed in Japanese Patent Application Laid-Open No.7-260741, there is a problem in that a concentration of oxygen to be removed can not be quantitatively and accurately measured. The measuring error in the exhaust gas components is affected by component of oxygen which can not be accurately removed. Further, the sensor of Japanese Patent Application Laid-Open No.7-260741 has a problem in that it is difficult to measure a very small amount of exhaust gas components because it can not perform two-step measurement, that is, removing of oxygen and then measuring the exhaust gas components.

Furthermore, when a plurality of solid electrolyte layers are laminated up to a certain amount of thickness so as to provide many functions, there occurs a problem that high response is difficult to be obtained because the gas to be measured is difficult to pass through the porous solid electrolyte layers. Quick heat-up of the sensing part is also difficult to be realized.

In regard to combustion control in a vehicle, the system has an oxygen sensor and an air-to-fuel ratio sensor, but does not have any on-board sensor capable of accurately and stably measuring exhaust gas components. Therefore, it is impossible to directly measure nitrogen oxide and hydrocarbon in order to reflect the combustion control.

SUMMARY OF THE INVENTION

An object of the present invention is to provide a multilayer gas component measuring apparatus having a good responsive characteristic with high reliability and easy fabrication.

According to the present invention, since there is no measurement chamber and no gas passage in each of laminated layers, number of the starting points of cracks under heating condition at manufacturing or using the sensor can be reduced and as a result occurrence of the cracks can be suppressed. Quick heat-up of the sensor is also abstained.

Further, since there is no structures such as a measurement chamber and a gas passage in each of laminated layers, the laminated body is easily formed by laminating the green sheets and/or through a printing method.

Further, by using a plurality of solid electrolyte layers including gas-penetrative solid electrolyte layers, it is possible to accurately remove oxygen component and to accurately measure exhaust gas components based on the above-mentioned two-step measurement.

Further, since the plurality of layers can be thinly laminated through the printing method, the problem of deterioration in gas penetration can be avoided though the plurality of gas-penetrative solid electrolyte layers are used.

Furthermore, in a case where the multilayer exhaust gas component sensor in accordance with the present invention is applied to a waste incinerating facility or a vehicle, since a very small amount of exhaust gas components such as $NO_X$ and HC can be directly measured, detailed combustion control to reduce the exhaust gas components can be performed.

DESCRIPTION OF THE PREFERRED EMBODIMENTS

Embodiments of the present invention will be described in detail, referring to accompanied figures. Description will be made below on examples of measuring mainly nitrogen oxides ($NO_X$) as exhaust gas components. Wherein similar parts in each of the accompanied figures are identified by the same reference characters.

Figure 1:
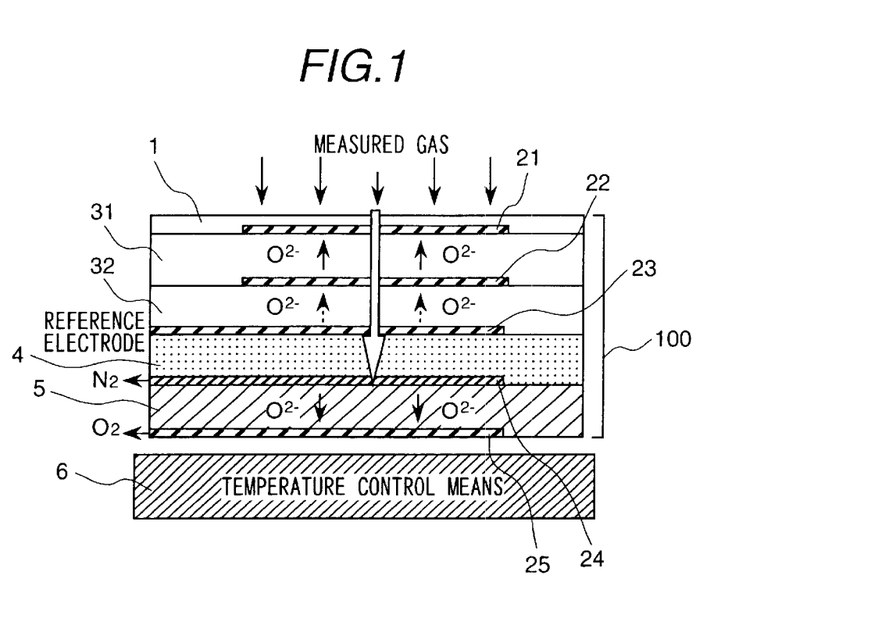
FIG. 1 is a cross-sectional view showing a first embodiment of a multilayer exhaust gas component sensor in accordance with the present invention.

FIG. 1 is a cross-sectional view showing a first embodiment of a gas component measuring apparatus (hereinafter, a multilayer exhaust gas component sensor will be particularly explained) in accordance with the present invention.

Initially, the structure of a sensor will be described.

In order from the top of the laminated layer body, the laminated layer body comprises a porous electrode protecting film 1, a first oxygen pump anode 21, a porous solid electrolyte layer 31, a first oxygen pump cathode 22, a porous solid electrolyte layer 32, an oxygen reference electrode 23, a porous electric insulating layer 4, a second oxygen pump cathode 24, a closely-compacted (dense) solid electrolyte layer 5 and a second oxygen pump anode 25. The laminated layer body is placed in contact with or near a temperature control means 6. FIG. 1 is an explanatory view in a case where the laminated layer body is placed near the temperature control means. The combination of the laminated layer body and the temperature control means 6 is called as a gas sensing portion. The structure of the gas sensing portion does not have any vacant chamber which a conventional exhaust gas component sensor has. Although the anode and the cathode in each of the electrode means are distinguished in order to make it easy to understand explanation, roles of these electrodes may be partially exchangeable depending on method of using the sensor.

Although a sintered solid electrolyte generally contains holes inside even if it is closely compacted without gas permeability, the word "porous" here means a property that such holes are communicated with one another to form gas-leaking paths. In this meaning, the porous solid electrolyte has a gas permeability, and the degree depends on a porosity. Although the gas permeability is increased as the porosity is increased, the mechanical strength is decreased. Therefore, the porosity is preferably below 50% in practical use.

Details and operation of each of the components will be described below.

The porous electrode protecting film 1 may be formed of, for example, a porous alumina film having a thickness of several tens micrometers. The porous electrode protecting film makes the gas to be measure diffuse and permeate, and at the same time prevents the electrode from being separated. Further, the porous electrode protecting film 1 serves to limit the diffusion rate of the gas to be measured so that an amount of oxygen removed by the first oxygen pump, to be described next, does not exceed a pump capacity.

The porous solid electrolyte layer 31, the anode 21 and the cathode 22 compose a cell of the first oxygen pump. The anode 21 and the cathode 22 are required to not hinder the gas from moving illustrated by an arrow in the figure. As a method of satisfying this requirement, an area of each of the electrodes 21, 22 is set to such a value as to hinder the gas from permeating not so much. However, the area of the electrode can not reduced so small because the area affects on the S/N ratio of the output of the sensor. Therefore, by using electrodes having a gas-permeability for the electrodes themselves, movement of the gas can be easily secured. As the electrode having a gas-permeability, a porous electrode, an electrode having cracks formed thermally or electrically or an electrode having a gas permeable portion formed through patterning may be used. As the material of the electrode used is a catalytic material which accelerates ionizing oxygen molecules or the inverse reaction. Metallic materials are one of the examples. The thickness of the electrodes, such as platinum, is exaggeratingly illustrated in the figure, but it is, for instance, about 10 $\mu$m. The area of the electrode is preferably about 10 mm$^2$. On the other hand, zirconia partially stabilized with yttria (YSZ) can be used for the porous solid electrolyte layer 31. Zirconia solid electrolyte heated up to above 700° C. works to pump oxygen ions inside the solid electrolyte by applying a voltage between the both ends. This phenomenon is known as an oxygen pumping action. Since the present invention uses a porous solid electrolyte having gas permeability for the solid electrolyte layer, it is unnecessary to form a measurement chamber and a gas passage in the solid electrolyte layer. Since the solid electrolyte layer itself can serve as both of a measurement chamber and a gas passage at a time, number of starting points of occurrence of cracks can be substantially reduced.

A porous solid electrolyte is sometimes used as a coating material having a gas permeability. On the other hand, the present invention is characterized by the point that the porous solid electrolyte is applied to an exhaust gas component sensor as a functional material having oxygen pumping action. In order to using the oxygen pumping action, electrode means are provided on the top surface and the bottom surface in the laminating direction of the porous solid electrolyte in accordance with the present invention.

The cathode 22, the porous solid electrolyte layer 32 and the oxygen reference electrode 23 compose a second oxygen pump for measuring an oxygen concentration. The material similar to the material in the first oxygen pump may be used for each of the components. The second oxygen pump is used for detecting and controlling an oxygen concentration in the gas after removing oxygen by the first oxygen pump. In the first oxygen pump, oxygen in the gas to be measured is removed so that the oxygen concentration becomes a constant value within a range that $NO_X$ is not decomposed. Therefore, it is preferable that the amount of oxygen removed in the first oxygen pump is accurately controlled. The pumping capacity of the first oxygen pump can be controlled by using the second oxygen pump so that difference between the oxygen concentration after being removed by the first oxygen pump and the oxygen concentration in the vicinity of the oxygen reference electrode 23 becomes a constant concentration difference. Because the oxygen concentration in the vicinity of the oxygen reference electrode 23 is regarded to be nearly constant as to be described below, an oxygen concentration can be measured from the amount of oxygen removed by the first oxygen pump.

The gas to be measured passed through the first oxygen pump arrives at the oxygen reference electrode 23. The oxygen concentration is largely reduced by the first oxygen pump, but the remaining oxygen is gradually supplied to the oxygen reference electrode 23. On the other hand, since the second oxygen pump always pumps oxygen to the cathode 22, the oxygen concentration in the vicinity of the oxygen reference electrode is kept nearly constant. It is known that relationship between oxygen concentrations at both ends of a solid electrolyte layer and a voltage follows Nernst equation (Equation 1).

$$E=(RT/4F)\ln[P1/P2] \qquad \text{(Equation 1)}$$

where E: voltage
R: gas constant
T: absolute temperature
F: Faraday constant
P1, P2: partial pressure of oxygen Since the logarithm of oxygen concentrations determines the voltage, the oxygen concentration can be regarded as practically constant even if an oxygen concentration of the oxygen reference electrode 23 is not accurately constant. In FIG. 1, the oxygen reference electrode 23 has a pattern portion connected to the external in a part of the electrode. By doing so, a minute amount of oxygen can be exchanged with the external using the gas permeability of the electrode to suppress an excessive change in the oxygen concentration in the vicinity of the oxygen reference electrode 23. Since oxygen is not accumulated in the electrode excessively, it is possible to prevent the electrode from being ruptured caused by erroneous operation of the sensor. Of course, the pattern portion may be omitted if the remaining oxygen concentration in the gas to be measured can be controlled so as to always balance with the pumping capacity of the second oxygen pump. Similarly to the case of the first oxygen pump, the gas is not hindered from moving by employing the gas-permeable materials in the cathode 22, the solid electrolyte layer 32 and the oxygen reference electrode 23, respectively.

The porous electric insulating layer 4 electrically insulates the first oxygen pump and the second oxygen pump from a third oxygen pump which will be described later. Since the porous electric insulating layer 4 also has a gas-permeability, the gas to be measured is not hindered from moving.

The cathode 24, the closely-compacted solid electrolyte layer 5 and the anode 25 compose the third oxygen pump. When oxygen is further removed from the gas to be measured arriving at the cathode 24, a decomposition reaction of $NO_X$ shown by (Equation 2) is produced because the oxygen concentration is already reduced. A catalytic material accelerating the decomposing reaction of $NO_X$ is used for the cathode 24. Examples of the metallic materials are platinum, rhodium and the like. A metallic material, such as platinum, may be used to the anode 25. Since $NO_X$ is decomposed mainly at the cathode 24, the solid electrolyte layer 5 does not need to have gas-permeability. Therefore, the closely-compacted zirconia solid electrolyte commonly used may be used for the solid electrolyte layer 5. In detail, the zirconia partially stabilized with yttria (YSZ) may be used. Since an amount of pumping current of the third oxygen pump depends on an $NO_X$ concentration according to (Equation 2), the concentration of $NO_X$ of the exhaust gas component can be measured.

$$NO_X \rightarrow (1/2)N_2 + (x/2)O_2 \quad \text{(Equation 2)}$$

N: nitrogen atom

O: oxygen atom

As the result of operation of the third oxygen pump, nitrogen and oxygen are accumulated at the cathode 24 and the anode 25, respectively. Each of the electrodes has a pattern portion communicated to the external so that the accumulated nitrogen or oxygen is gradually released to the external. Since in general the closed-compact solid electrolyte is mechanically stronger than the porous solid electrolyte, the solid electrolyte layer 5 composing the third oxygen pump also serves as a supporting member for the strength of the laminated layer body 100. The effect can be further improved by increasing the thickness of the solid electrolyte layer 5 compared to those of the other layers. Since the solid electrolyte layer 5 does not allow the gas to pass through, effect of change in the thickness on the responsive characteristic of the sensor is small.

The laminated layer body 100 composed of the elements described above is placed at a position near a temperature control means 6. Otherwise, the laminated layer body 100 may be directly mounted on the temperature control means 6. A heater, for example, formed by covering a platinum heater with alumina may be used for the temperature control means 6. The temperature control means 6 heats the laminated layer body up to a temperature at which each of the oxygen pumps described above can be operated. There are various kinds of method usable for the temperature control. One example of the methods is that a resistance value of any one of the electrodes and/or zircoia layers is measured to obtain an actual temperature, and current of a heater is controlled based on the obtained temperature. It is possible perform time sharing processing to measure the resistance value during an interval between operations of the sensor signal sensing.

Figure 2:
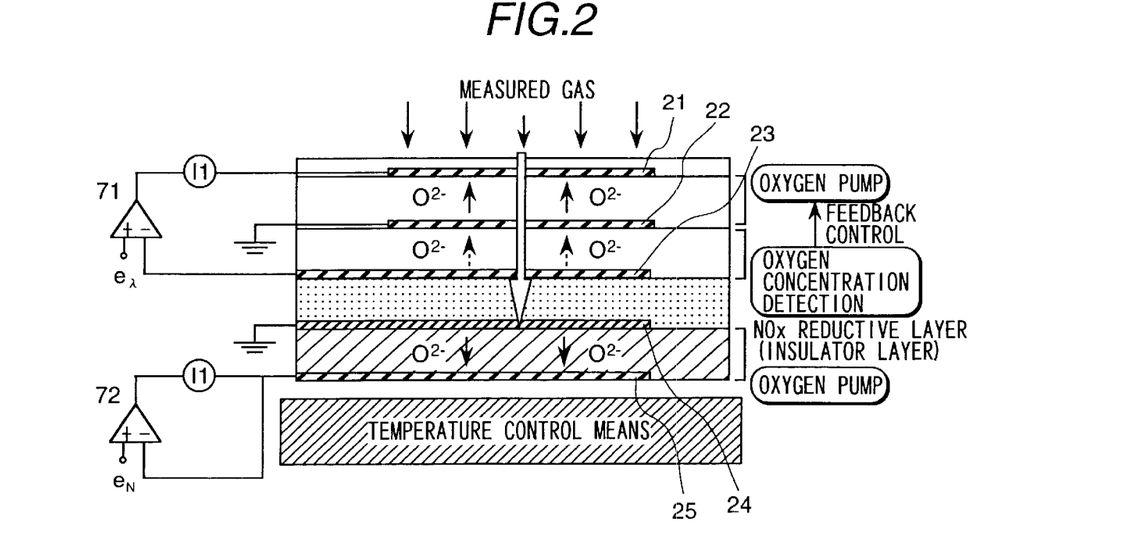
FIG. 2 is a view explaining operation of the first embodiment of the multilayer exhaust gas component sensor in accordance with the present invention.

FIG. 2 explains an example of operation of the first embodiment of the multilayer exhaust gas component sensor ($NO_X$ sensor) in accordance with the present invention. An operational amplifier 71 controls the current I1 of the first oxygen pump so that the voltage between the both end electrodes of the second oxygen pump becomes a constant value $e_\lambda$. The oxygen concentration in the vicinity of the reference electrode 23 is kept constant by comparing with the oxygen concentration in the vicinity of the cathode 22. When the oxygen concentration in the gas to be measured is changed, corresponding to the change the oxygen concentration in the vicinity of the cathode 22 is changed and the voltage between the both ends of the electrodes of the second oxygen pump. The pumping amount of the first oxygen pump is changed so as to compensate the change in the voltage between the both ends of the electrodes of the second oxygen pump. By the operation described above, the oxygen concentration in the gas to be measured can be accurately reduced to a certain value within a range not decomposing $NO_X$. Because the current I1 is changed depending on the oxygen concentration in the gas to be measured, the oxygen concentration in the gas to be measured can be measured from the current value I1. An operational amplifier 72 controls so that the a voltage of the anode 25 to the cathode 24 of the third oxygen pump becomes a constant value $e_N$. The gas to be measured moved up to the cathode 24 is in a state of reduced oxygen concentration within a range not decomposing $NO_X$. Under such a condition, when the oxygen concentration is further reduced under the catalytic operation of the cathode 24, the deoxidizing reaction of $NO_X$ according to (Equation 2) occurs. The oxygen produced by the reaction is transferred to the anode 25 by the third oxygen pump. That is, the value of the current I2 is changed corresponding to the $NO_X$ concentration. As a result, the concentration of $NO_X$ as the exhaust gas component can be measured from the value of the current I2. In the above, the voltage values $e_\lambda$ and $e_N$ may be kept constant or changed depending on the measurement condition. These operation may be performed using a control system such as a microcomputer externally provided.

Figure 3:
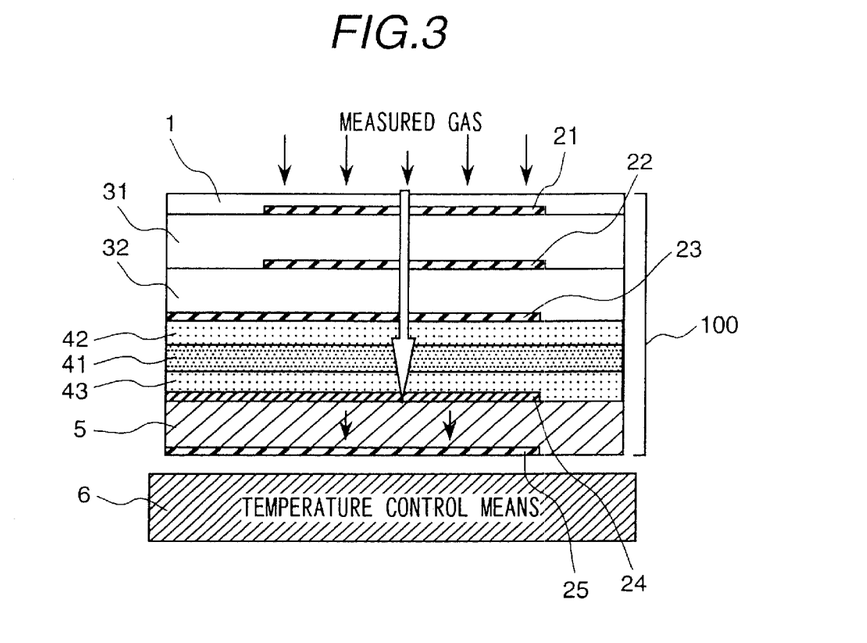
FIG. 3 is a cross-sectional view showing a second embodiment of a multilayer exhaust gas component sensor in accordance with the present invention.

FIG. 3 is a cross-sectional view showing a second embodiment of a multilayer exhaust gas component sensor in accordance with the present invention. This embodiment is characterized by the point that the porous electric insulating layer 4 in FIG. 1 is composed of three layers 41, 42 and 43. The thermal properties (thermal expansion coefficient and the like) of the porous electric insulating layers 42 and 43 are set to middle values between the thermal properties of the porous electric insulating layer 41 and the thermal properties of the upper and the lower solid electrolyte layers, respectively. Although there is generally a difference between the insulating layer 41 and the solid electrolyte layer 32 or 5 in the thermal expansion coefficient, thermally caused deformation of the laminated layer body 100 can be moderated by inserting the porous electric insulating layers 42 and 43. As the result, the laminated layer body 100 can be prevented from being broken under repetitive temperature change for a long time. In adjusting the thermal properties, there is no problem even if the insulating layers 42 and 43 have an electric conductivity in a some degree. This is because that the middle insulating layer 41 can ensure the electric insulation. When the insulating layers 42 and 43 are symmetrically formed of the same material, the insulating layer combined of the three layers does not bend as a bimetal, and the effect of moderating the thermal deformation becomes large. The other structures in regard to the functions of the sensor are not different from those of FIG. 1 and FIG. 2.

Figure 4:
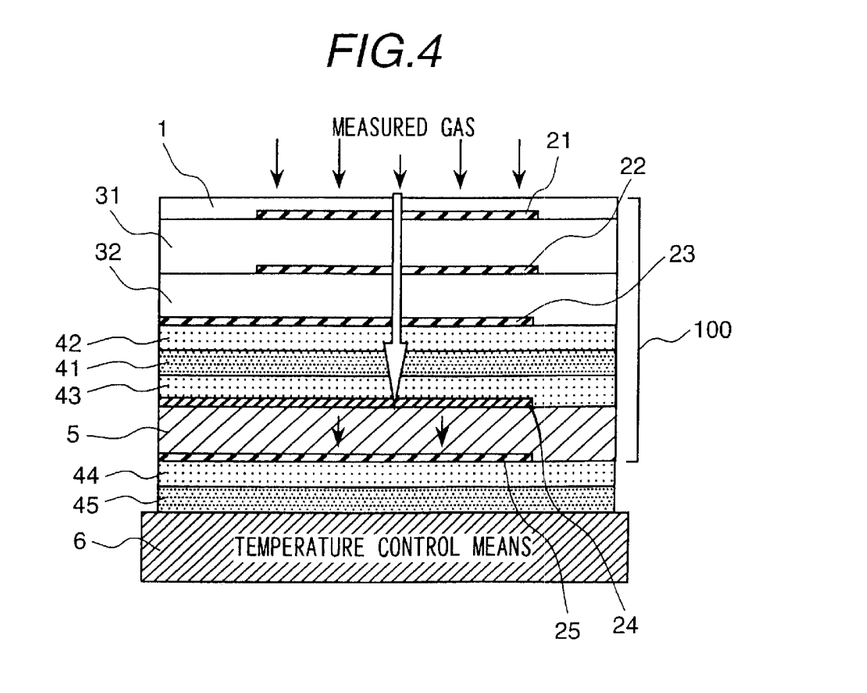
FIG. 4 is a cross-sectional view showing a third embodiment of a multilayer exhaust gas component sensor in accordance with the present invention.

FIG. 4 is a cross-sectional view showing a third embodiment of a multilayer exhaust gas component sensor in accordance with the present invention. This embodiment is characterized by the point that electric insulating layers 44 and 45 are inserted between the laminated layer body 100 and the temperature control means 6 of FIG. 3. The thermal properties (linear expansion coefficient and the like) of the electric insulating layers 44 and 45 are set to middle values between the thermal physical properties of the laminated layer body 100 and the temperature control means 6. Thereby, thermally caused deformation of the sensing portion can be moderated, and as the result, the laminated layer body 100 can be prevented from being broken under repetitive temperature change for a long time. Although FIG. 4 shows the case where the two electric insulating layers are inserted between the laminated layer body 100 and the temperature control means 6, of course it is possible to change number of layers to be inserted. Since the gas does not flow between the laminated layer body 100 and the temperature control means 6, the electric insulating layers 44, 45 can be made of a closely-compacted (dense) material. Further, from the.same reason, there is no trouble even if the number of layers to be inserted is increased. The other structures in regard to the functions of the sensor are not different from those of FIG. 1 and FIG. 2.

Figure 5:
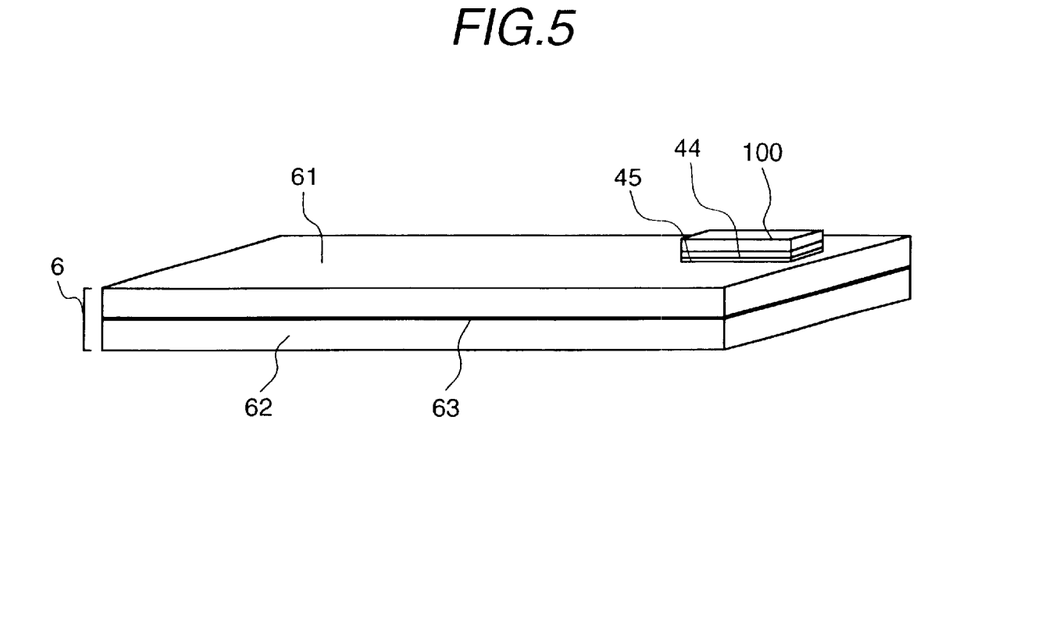
FIG. 5 is a view showing the overall structure of the third embodiment of the multilayer exhaust gas component sensor in accordance with the present invention.

FIG. 5 show a feature of the structure of the third embodiment of the multilayer exhaust gas component sensor in accordance with the present invention. The laminated layer body 100 is mounted on an end portion of an upper surface of the plate type temperature control means 6 through the electric insulating layers 44, 45. The temperature control means 6 is formed by interposing a layer including a heater wire (or a heater pattern using platinum or the like) 63 between insulator layers 61, 62 made of alumina or the like. By making the size of the laminated layer body sufficiently smaller than the size of the temperature control means, the laminated layer body can be heated up to a preset operating temperature in a short time. In addition, unevenness of temperature (temperature gradient) inside the laminated layer body can be reduced. The laminated layer body 100 and the electric insulating layers 44, 45 can be manufactured by laminating plate-shaped green sheets, press fitting the laminated layers, and then baking the press fit layers. Otherwise, the multilayer exhaust gas component sensor can be also manufactured by laminating partially baked layers through an adhering layer such as an adhesive one another, and then further baking them. It is effective that the electric insulating layers 44, 45 and the individual layers of the laminated layer body 100 including electrodes are printed successively on the temperature control means 6 formed by laminating the green sheets and the heater pattern, and then they are baked to manufacture the multilayer exhaust gas component sensor. Since the multilayer exhaust gas component sensor in accordance with the present invention does not have any measurement chamber and any gas passage, it is easy to laminate the individual layers including electrodes.

Although FIG. 5 shows the example of mounting the laminated layer body 100 on the plate-shaped ceramic member, the member of the base plate is not always necessary to be a plate-shape. For example, the laminated layer body 100 may be mounted on a member formed in a sack-tube shape known in the field of oxygen sensor. It is easy to print on a curved surface by using a printing technique such as silk screen printing. In this case, if the member formed in the sack-tube shape is made of a solid electrolyte, the function of the closely-compacted solid electrolyte layer 5 may be served using the member formed in the sack-tube shape instead of the closely-compacted solid electrolyte layer 5 composing the laminated layer body.

Figure 6:
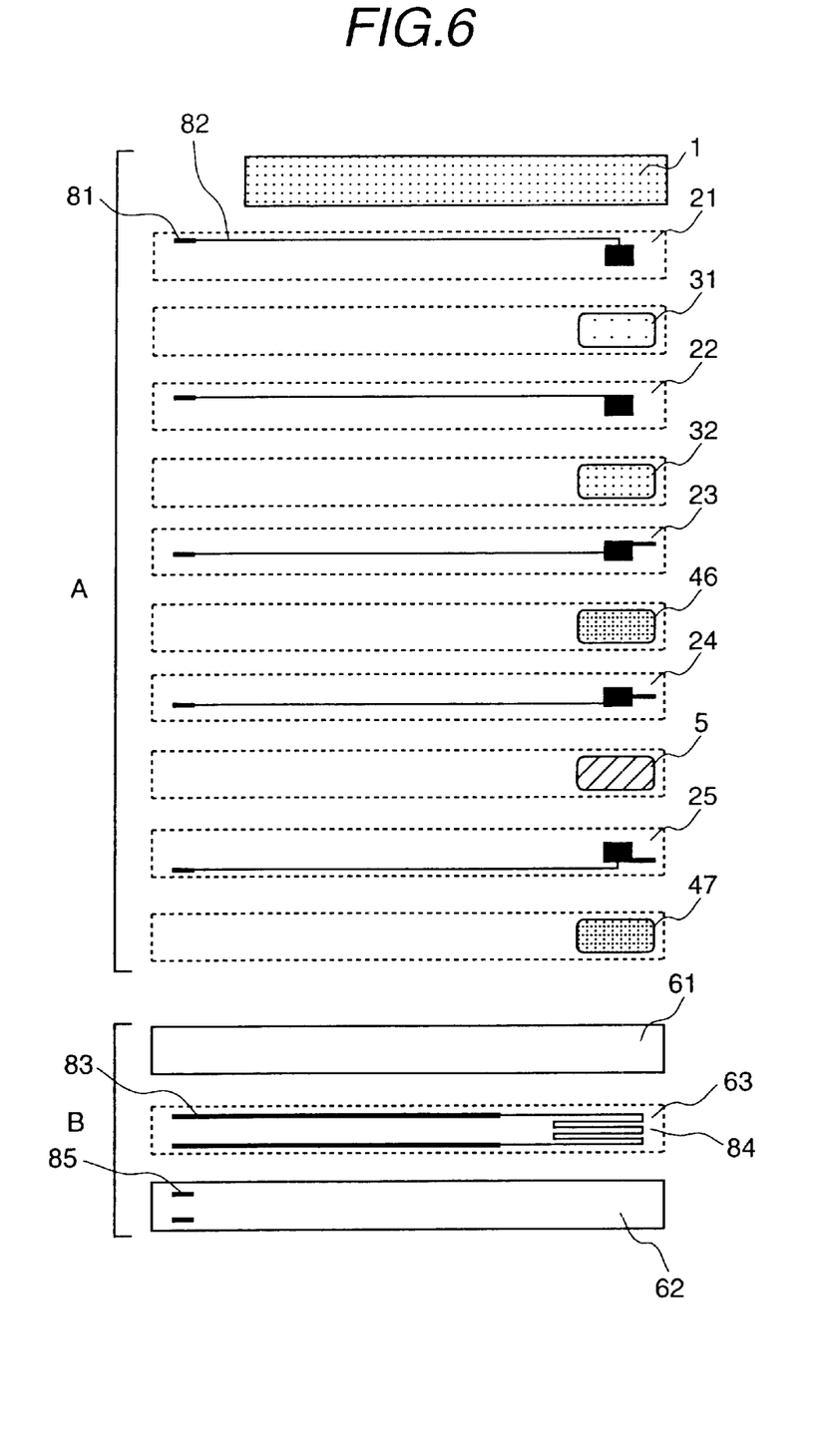
FIG. 6 is a view explaining a method of constructing the multilayer exhaust gas component sensor in accordance with the present invention.

FIG. 6 shows an example of a laminating structure of the multilayer exhaust gas component sensor in accordance with the present invention. The layers are laminated in order of, from the bottom, an alumina layer (green sheet) 62, a platinum heater pattern 84, an alumina layer (green sheet) 61, an insulator layer 47, an electrode pattern 25, a closely-compacted (dense) zirconia layer 5, an electrode pattern 24, a porous insulating layer 46, an electrode pattern 23, a porous zirconia layer 32, an electrode pattern 22, a porous zirconia layer 31, an electrode pattern 21 and a porous electrode protective film (alumina) 1. In order to reduce thermal deformation, it is preferable that the insulating layers 46, 47 are formed of a member having a middle value of the thermal expansion coefficient between the thermal expansion coefficient of alumina and the thermal expansion coefficient of zirconia (YSZ). Otherwise, a plurality of layers may be laminated as shown in FIG. 3 and FIG. 4. The reference character 81 indicates a terminal portion (a pad) of the electrode, the reference character 82 indicates an electrode wire, the reference character 83 indicates a heater wire, the reference character 84 indicates a heater, and the reference character 85 indicates a terminal portion (a pad) of the heater. The terminal portion 85 of the heater provided in the alumina layer 62 can be arranged through a through hole from the heater 83. The portion B in FIG. 6 can be fabricated mainly with green sheets, and the portion A can be fabricated through a printing method. The portion A can be also printed and baked on the top portion of the pre-laminated portion B of the temperature control means using the insulating layer 47 as a adhering layer.

When a plurality of solid electrolyte layers are laminated to a certain thickness, the gas to be measured generally becomes difficult to pass through and accordingly a high responsive characteristic is difficult to be obtained. However, in the multilayer exhaust gas component sensor in accordance with the present invention, the plurality of layers can be laminated in a thin thickness through the printing method. By doing so, although very small amount of exhaust gas components can be accurately sensed by using the plurality of solid electrolyte layers, the responsive characteristic can not be deteriorated.

Figure 7:
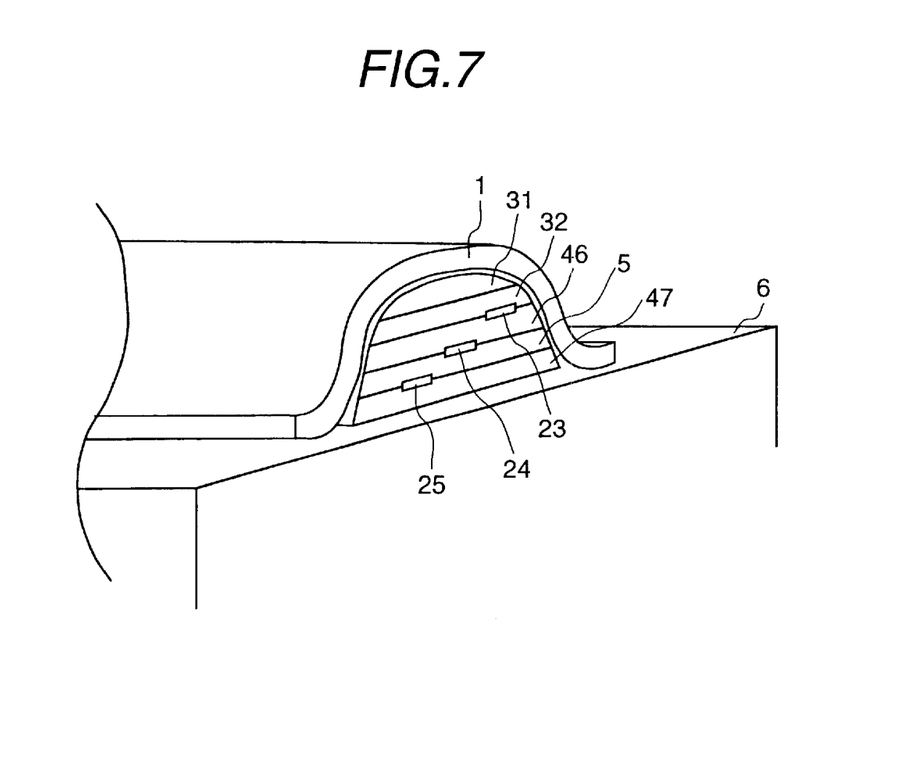
FIG. 7 is a view explaining a coating of side surface of the laminated body with a protective film having an electric insulating property.

In the case of FIG. 5 in which green sheets are laminated, the side surfaces of the solid electrolyte layers are exposed to the atmosphere. On the other hand, in the case of FIG. 6 where the printing method is used, the side surfaces of the solid electrolyte layers can be covered with the electrode protecting film 1 as shown in FIG. 7. The reference characters 23, 24 and 25 in FIG. 7 indicate portions of the electrode patterns opening outside the laminated layer body. Since the size of the electrode protecting film 1 can be determined so as to not cover the opening portions of the electrodes, the reaction gas accumulated in the porous electrolyte can be released to the external. According to FIG. 7, since the main portion of the outer surface of the gas sensing portion can be covered with the protecting film having an electric insulating property, it is possible to avoid a failure such as an electrical short-circuit caused by, for example, attaching of extraneous objects on the side surfaces of the laminated layer body during using the sensor. Of course, it is possible that a protecting film having a electric insulating property is separately placed to cover the side surfaces of the laminated layer body.

Figure 8:
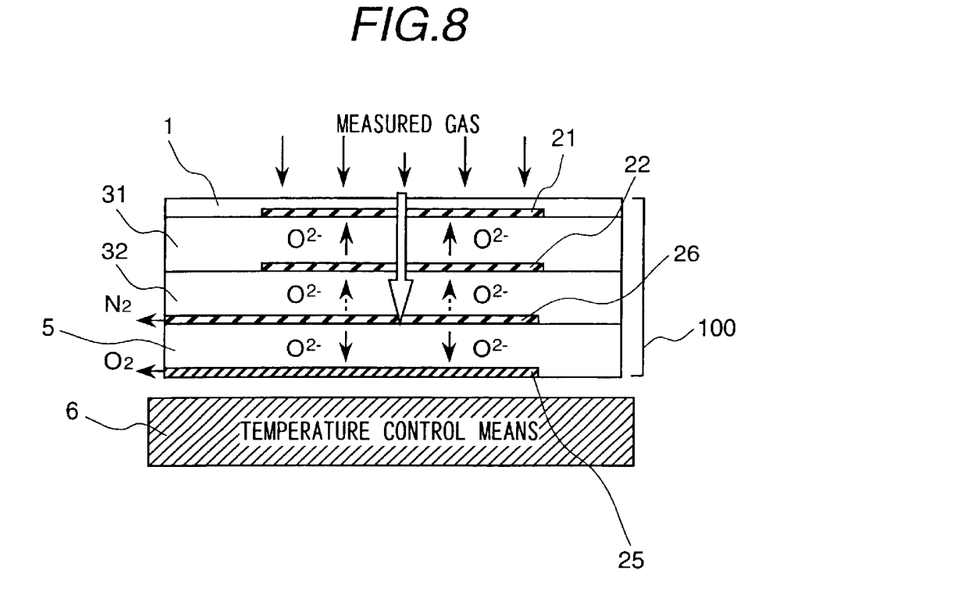
FIG. 8 is a cross-sectional view showing a fourth embodiment of a multilayer exhaust gas component sensor in accordance with the present invention.
Figure 9:
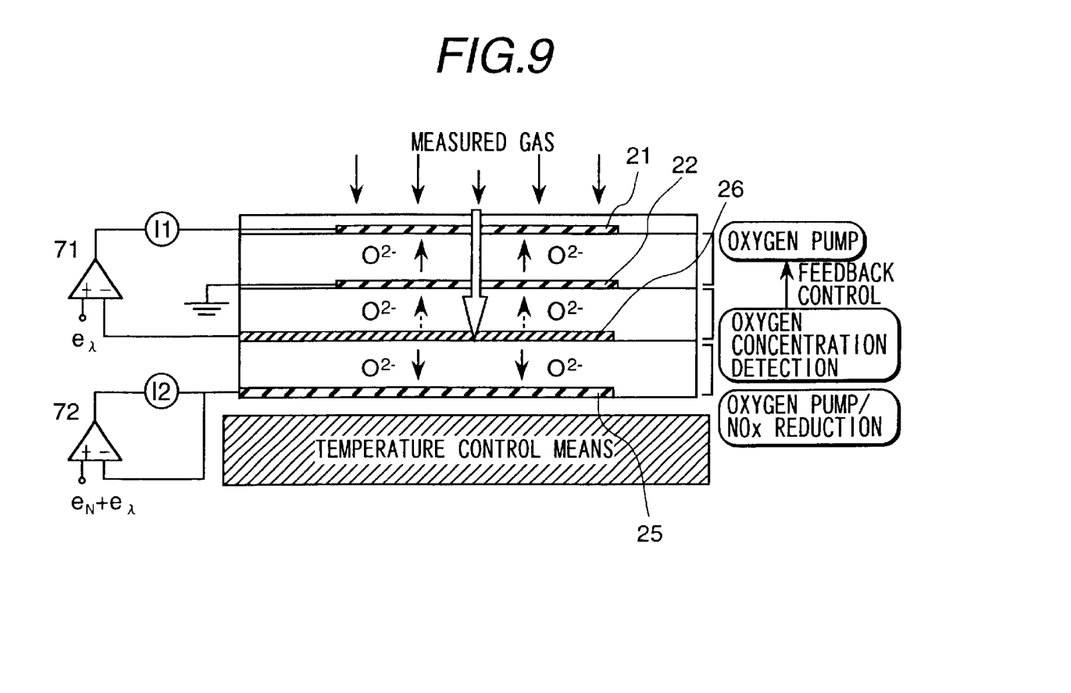
FIG. 9 is a view explaining operation of the fourth embodiment of the multilayer exhaust gas component sensor in accordance with the present invention.

FIG. 8 is a cross-sectional view showing a fourth embodiment of a multilayer exhaust gas component sensor in accordance with the present invention. FIG. 9 explains an example of the operation as the sensor. This embodiment is characterized by the point that number of the layers is reduced by eliminating the porous electric insulating layer of FIG. 1 and putting the electrodes 23, 24 to an electrode 26 together. The gas to be measured can move easier than in the embodiments described above to improve the responsive characteristic of the sensor. After the gas to be measured passes through the porous electrode protecting film 1, oxygen in the gas is removed by the oxygen pumping action of the porous electrolyte layer 31 composing the first oxygen pump. The amount of oxygen removed here is within a range of not decomposing $NO_X$. As shown in FIG. 9, the concentration of oxygen remaining the gas to be measured can be controlled using an operation amplifier 71 so as to become a constant value to the oxygen concentration in the vicinity of the reference electrode. In more detail, the current I1 is controlled so that the voltage between the both ends of the second oxygen pump becomes a constant value $e_\lambda$. On the other hand, the oxygen concentration in the vicinity of the oxygen reference electrode is kept nearly constant by the oxygen pumping action of the porous solid electrolyte layer 32 composing the second oxygen pump and by the pumping action of the closely-compacted solid electrolyte layer 5 composing the third oxygen pump. The oxygen concentration in the vicinity of the oxygen reference electrode is adjusted to a concentration capable of occurring decomposing reaction of $NO_X$. The oxygen reference electrode 26 is made of a catalytic material such as platinum or rhodium which accelerates ionization of oxygen and at the same time accelerates deoxidizing reaction of $NO_X$. An operational amplifier 72 controls a voltage between the both ends of the third oxygen pump cell so as to becomes a constant value $e_N$. When deoxidizing reaction of $NO_X$ occurs, pumping amounts of the second and the third oxygen pumps are changed. In regard to the second oxygen pump, the concentration of deoxidizing reaction of $NO_X$ to be measured is of an order of several hundreds ppm, and the concentration of oxygen produced by the deoxidizing reaction is very small compared to the pumping amount of the first oxygen pump. Therefore, the oxygen produced by the deoxidizing reaction of $NO_X$ does not largely affect on the role of the oxygen reference electrode for controlling operation of the first oxygen pump. On the other hand, in regard to the third oxygen pump, the value of the pump current I2 is small and nearly constant when the $NO_X$ concentration is zero, and the current I2 is increased when the $NO_X$ concentration increases. Therefore, the $NO_X$ concentration can be calculated from the value of the pump current I2. If an atmospheric condition making the $NO_X$ concentration zero is known in advance, the $NO_X$ concentration can be calibrated by subtracting a bias value from a sensor output (the value of pump current I2).

Figure 10:
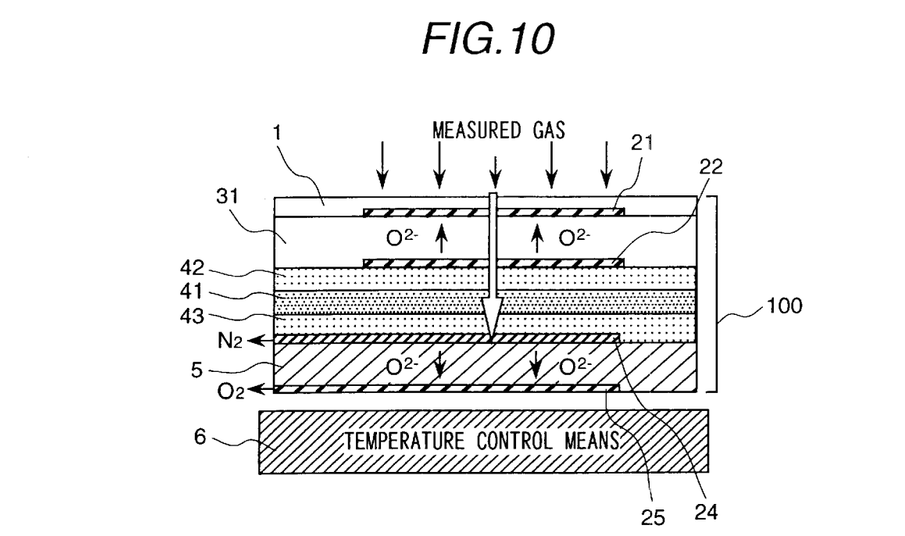
FIG. 10 is a cross-sectional view showing a fifth embodiment of a multilayer exhaust gas component sensor in accordance with the present invention.
Figure 11:
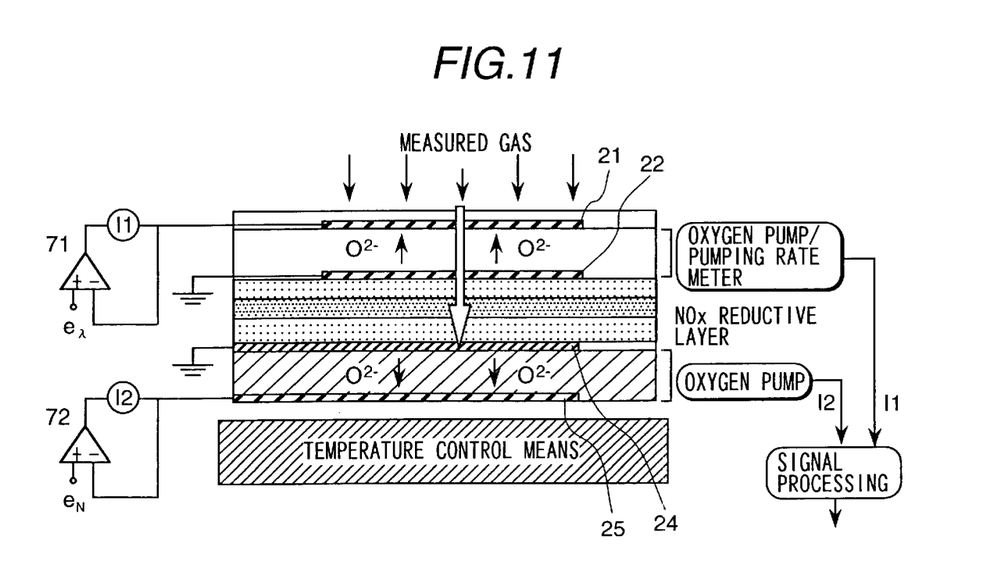
FIG. 11 is a view explaining operation of the fifth embodiment of the multilayer exhaust gas component sensor in accordance with the present invention.

FIG. 10 is a cross-sectional view showing a fifth embodiment of a multilayer exhaust gas component sensor in accordance with the present invention. FIG. 11 explains an example of the operation as the sensor. This embodiment is characterized by the point that number of the layers is reduced by eliminating the porous solid electrolyte layer 32 and the oxygen reference electrode 23 of FIG. 1 to make the gas to be measured easily move in the laminated layer body. Thereby, the responsive characteristic of the sensor can be improved. Further, comparing to the fourth embodiment of the present invention, there is no interference between the oxygen removal by the first oxygen pump and the function of the $NO_X$ deoxidization by the third oxygen pump. After the gas to be measured passes through the porous electrode protecting film 1, oxygen in the gas is removed by the oxygen pumping action of the porous electrolyte layer 31 composing the first oxygen pump. The amount of oxygen removed here is within a range of not decomposing $NO_X$. As shown in FIG. 11, an operational amplifier 71 controls so that the terminal voltage of the solid electrolyte layer 31 becomes a constant value $e_\lambda$. Since the current I1 is increased when the oxygen concentration in the gas to be measured is relatively high and decreased when low, the oxygen concentration can be obtained from an amount of the pump current I1. The gas to be measured passing through the porous electric insulating layers 41, 42 and 43 arrives an electrode 24. The electrode 24 is made of a catalytic material such as platinum or rhodium which accelerates ionization of oxygen and at the same time accelerates deoxidizing reaction of $NO_X$. The operational amplifier 72 controls a voltage between the both ends of the third oxygen pump cell so as to becomes a constant value $e_N$. When deoxidizing reaction of $NO_X$ occurs by the operation of the third oxygen pump, the value of the current I2 is changed. Therefore, a concentration of $NO_X$ can be obtained from the value of the current I2. This embodiment may be difficult to precisely control the remaining oxygen concentration, it may be difficult to directly monitor whether or not the remaining oxygen concentration after passed through the first oxygen pump is within the range not decomposing $NO_X$. However, if the removing amount of oxygen by the first oxygen pump is set to a slightly smaller value (smaller value of $e_N$), it is possible that the very small amount of $NO_X$ can be protected from being decomposed at the first oxygen pump. In this case, a relatively large bias is produced in the current I2 because the remaining oxygen concentration to the third oxygen pump is increased, but the bias of the current I2 of the sensor output can be corrected based on the current I1 which has a correlation with the remaining oxygen concentration.

Figure 12:
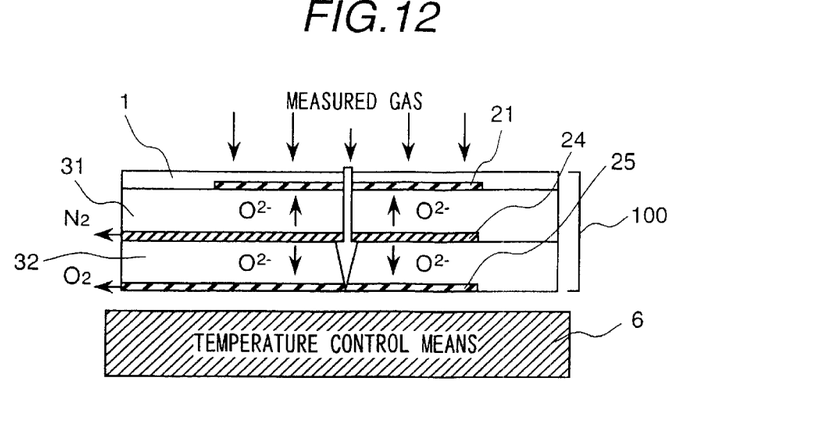
FIG. 12 is a cross-sectional view showing a sixth embodiment of a multilayer exhaust gas component sensor in accordance with the present invention.
Figure 13:
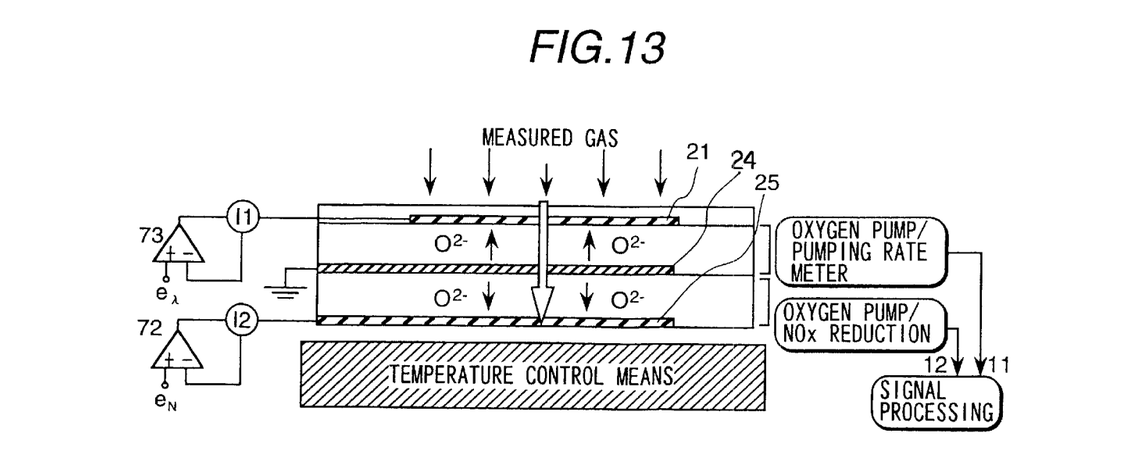
FIG. 13 is a view explaining operation of the sixth embodiment of the multilayer exhaust gas component sensor in accordance with the present invention.

FIG. 12 is a cross-sectional view showing a sixth embodiment of a multilayer exhaust gas component sensor in accordance with the present invention. FIG. 13 explains an example of the operation as the sensor. This embodiment is characterized by the point that the laminated layer body is composed of only the porous solid electrolyte layers 31, 32 and the corresponding electrodes. Since the number of the layers is greatly decreased, the gas to be measured can move easier to improve the responsive characteristic of the sensor. In addition, it is easy to fabricate the sensor since the number of the layers is small. It is also easy to set the baking condition because the laminated layer body is almost made of one kind of structural material. After the gas to be measured passes through the porous electrode protecting film 1, oxygen in the gas is removed by the oxygen pumping action of the porous electrolyte layer 31 composing the first oxygen pump. The amount of oxygen removed here is within a range of not decomposing $NO_X$. As shown in FIG. 12, an operational amplifier 73 controls so that the terminal voltage of the solid electrolyte layer 31 becomes a constant value $e_\lambda$. Since the current I1 is increased when the oxygen concentration in the gas to be measured is relatively high and decreased when low, the oxygen concentration can be obtained from an amount of the pump current I1. The electrode 24 is made of a catalytic material such as platinum or rhodium which accelerates ionization of oxygen and at the same time accelerates deoxidizing reaction of $NO_X$. The operation of the oxygen pump is similar to that of the case of FIG. 9, and in regard to signal processing, the $NO_X$ concentration can be measured similarly to the case of FIG. 11.

The porous solid electrolyte layer 31 removes oxygen in the atmosphere, and the porous solid electrolyte layer 32 deoxidizes and measures $NO_X$. Two-stage measurement required to measure a very small amount of exhaust gas components is performed by combining a plurality of porous solid electrolyte layers.

Figure 14:
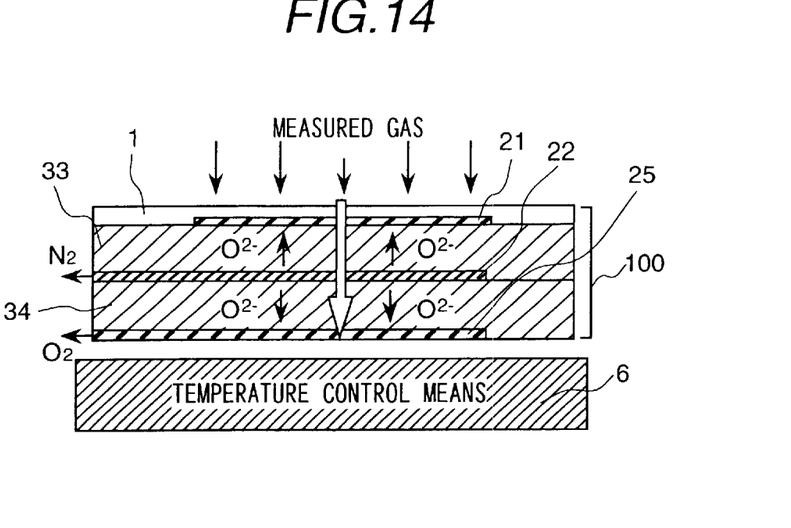
FIG. 14 is a cross-sectional view showing a seventh embodiment of a multilayer exhaust gas component sensor in accordance with the present invention.

FIG. 14 is a cross-sectional view showing a seventh embodiment of a multilayer exhaust gas component sensor in accordance with the present invention. This embodiment is characterized by the point that a catalytic material such as platinum or rhodium accelerating ionization of oxygen and deoxidizing reaction of $NO_X$ is mixed in the porous solid electrolyte layers. The porous solid electrolyte layer 33 is made of a material prepared by mixing a catalytic material accelerating the dissociation reaction of oxygen into a solid electrolyte such as zirconia (YSZ). The porous solid electrolyte layer 34 is made of a material prepared by mixing a catalytic material accelerating ionization of oxygen and deoxidizing reaction of $NO_X$ into a solid electrolyte. Although the operation as the element is the same as that of the embodiment of FIG. 13, in the present embodiment interference between the two oxygen pumps is reduced and the gas reaction can be effectively accelerated because ionization of oxygen and deoxidization reaction of $NO_X$ are progressed while the gas to be measured is passing through the porous solid electrolyte layers.

In the $NO_X$ sensors in accordance with the present invention, the measurement chamber and the gas passage contained in the conventional structure are replaced by the multilayer structure of the porous solid electrolytes. Therefore, the starting points of occurrence of large cracks can be eliminated, and at the same time the laminated layer body can be easily formed by the printing method. At the same time, by using the plurality of solid electrolyte layers having gas permeability, it is possible to accurately remove the oxygen component, to perform the two-stage measurement and to accurately measure the exhaust gas components.

Figure 15:
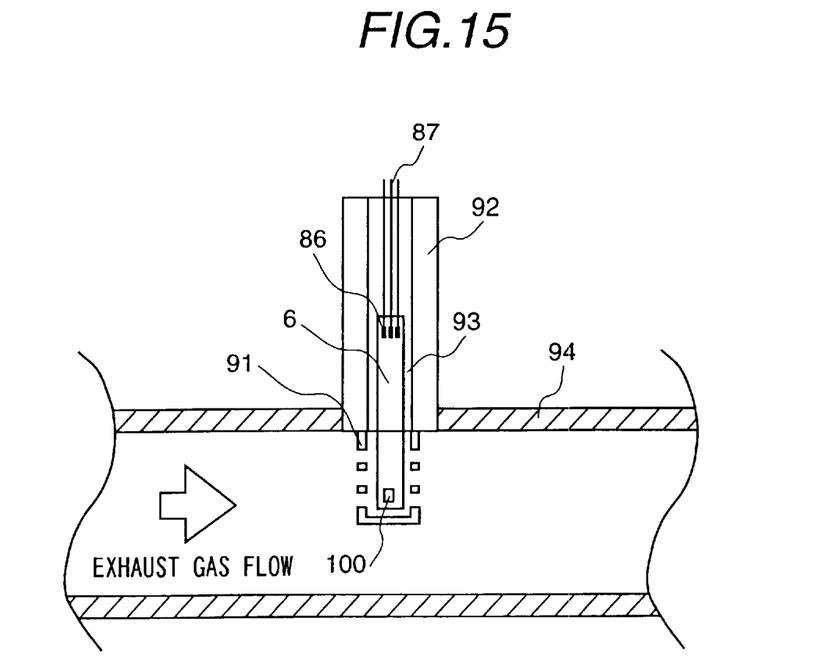
FIG. 15 is a view explaining mounting the multilayer exhaust gas component sensor in accordance with the present invention on an exhaust gas pipe.

FIG. 15 explains an example of mounting the multilayer exhaust gas component sensor in accordance with the present invention on an exhaust gas pipe of a waste incinerating facility or an engine. Referring to the figure, the reference character 100 is a laminated layer body of sensing element, the reference character 6 is a temperature control means supporting the laminated layer body, the reference character 86 is an electrode pad, the reference character 87 is a lead wire, the reference character 91 is a protective pipe, the reference character 92 is a member for reinforcing the sensor during handling, the reference character 93 is a gas sealing means and the reference character 94 is a pipe through which the gas to be measured flows. For the purpose of simplification, the detailed structure of each of the parts is omitted. For example, the protective pipe 91 may be a structure composed of a plurality of appropriately arranged pipes each having a plurality of holes necessary for gas to flow through. The munting method described above can be applied to a general exhaust pipe irrespective of a kind of system to which the sensor is applied.

Since zirconia (YSZ) can be operated under a temperature above 600° C., the exhaust gas component sensor in accordance with the present invention exerts the effect of stable operation under a high temperature condition such as a vehicle exhaust atmosphere. Of course, since the sensor has the temperature control means, the ion conductivity of the solid electrolyte can be ensured and the sensor can be stably operated under a low temperature condition. Therefore, by mounting the exhaust gas component sensor in accordance with the present invention on an exhaust gas pipe portion of an industrial facility requiring combustion control, it is possible to perform combustion control for reducing exhaust gas component under a wide atmospheric temperature range.

Figure 16:
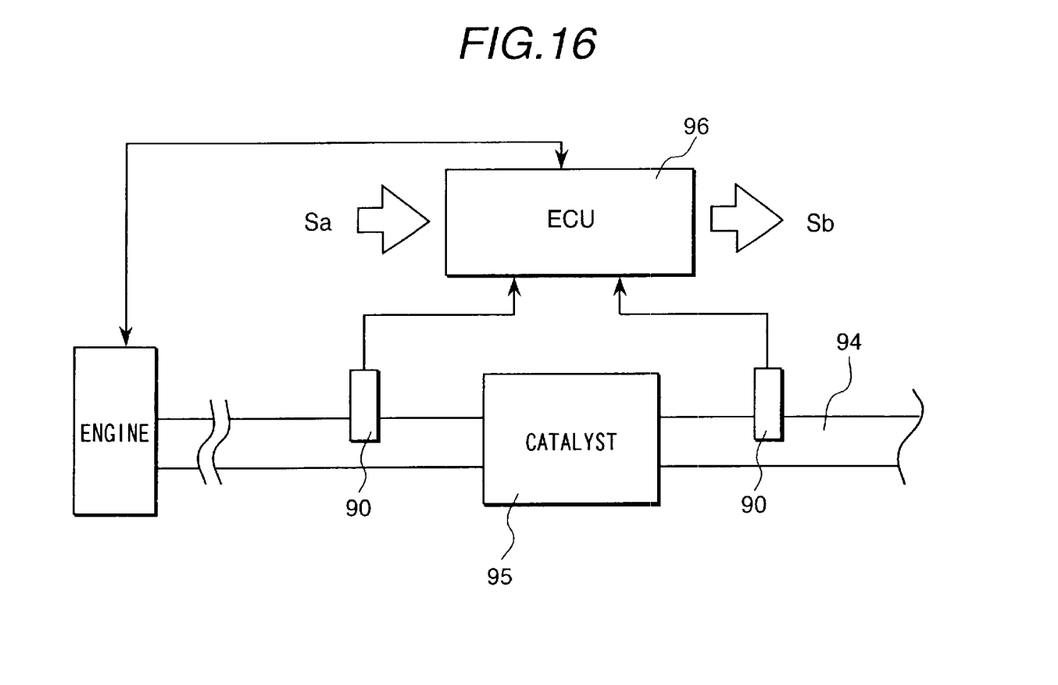
FIG. 16 is a view explaining an engine combustion control system of a vehicle using a multilayer exhaust gas component sensor in accordance with the present invention.

FIG. 16 explains an example of a feature of an exhaust gas component sensing and control system which is mounted on an exhaust pipe portion of a vehicle. The reference character 90 indicates a multilayer exhaust gas component sensor in accordance with the present invention mounted according to the method of FIG. 15 or the like; the reference character 95 indicates an $NO_X$ catalyst; the reference character 96 indicates an electronic control unit; the reference character Sa indicates input signals from other sensors, actuators, control units; and the reference character Sb indicates output signals to other sensors, actuators, control units. The electronic control unit 96 may be an engine control unit or a unit separately arranged at a position near the catalyst 95 or the sensor 90. The $NO_X$ catalyst 95 has a problem that the catalytic ability is saturated during using period or deteriorated with time. Therefore, the catalytic ability needs to be diagnosed. According to the system of FIG. 16, by comparing an output of the sensor in upstream of the catalyst with an output of the sensor downstream, it is possible to quantitatively diagnose whether or not $NO_X$ is decomposed. Further, an $NO_X$ concentration discharged in the atmosphere from the downstream side can be directly measured. Engine combustion control can be performed in detail since a very small amount of exhaust gas components can be directly sensed. The present invention can be also applied to a waste incineration facility.

Figure 17:
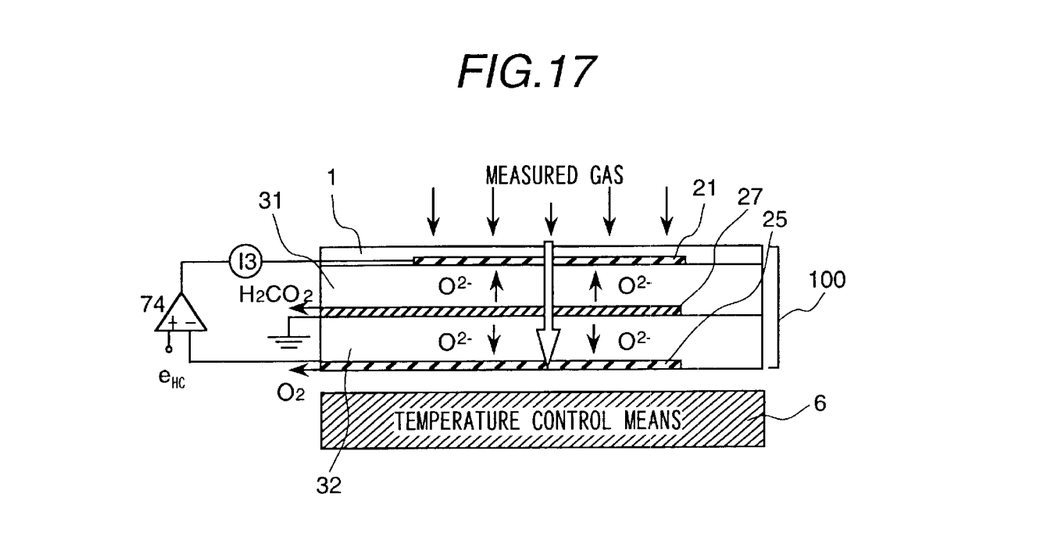
FIG. 17 is a cross-sectional view showing an eighth embodiment of a muiltilayer exhaust gas component sensor in accordance with the present invention.

FIG. 17 is a cross-sectional view showing an eighth embodiment of a multilayer exhaust gas component sensor in accordance with the present invention. This embodiment is a sensor for measuring hydrocarbon (HC) and not $NO_X$. An operational amplifier 74 controls so that the voltage between both ends of the solid electrolyte layer 32 becomes a constant value $e_{HC}$. Further, the porous solid electrolyte layer 31 supplies oxygen to the electrode 27 having a catalytic action. The same materials as in the case of the $NO_X$ sensor described above can be used for the solid electrolyte layers 31, 32 and the electrodes 21, 25. The characterized portion is the electrode 27 which is formed of a catalytic material to accelerate oxidizing and reducing reaction of HC. When oxygen is consumed by the catalytic reaction, a voltage of the electrode 27 to the electrode 25 is changed, and accordingly a current I3 flows so as to compensate the voltage. Therefore, an HC concentration can be detected from the current I3. As the present embodiment, by combining with the electrode having a catalytic action, the multilayer exhaust gas component sensor in accordance with the present invention can cope with sensing of various kinds of exhaust gas components, and can ensure accuracy and reliability of the sensor.

What is claimed is:

1. A measuring apparatus for measuring $NO_X$ and HC components, comprising:

a first solid electrolyte layer;

a second solid electrolyte layer, said first solid electrolyte layer and said second solid electrolyte layer being laminated without a vacant chamber and gas-permeable electrodes at both sides of said first and second solid electrolyte layers, wherein said first solid electrolyte layer is porous and is configured to remove at least part of oxygen in a gas passing through the first solid electrolyte layer by conducting current, whereby the apparatus is operative to deoxidize or oxidize $NO_X$ and HC components to be measured in the gas passed through said first solid electrolyte layer by conducting current to said second solid electrolyte layer, and to measure a concentration of said components based on the current conducted through said second solid electrolyte layer, and wherein said first and second solid electrolyte layer and said gas permeable electrodes constitute a body laminated on a heating device, in which said second solid electrolyte layer is arranged nearer to the heating device than said first solid electrolyte layer, whereby $N_2$ gas or $CO_2$ gas accumulated at one of the electrodes of said second solid electrolyte layer is released from a portion of the electrode exposed to the atmosphere at a side of the laminated body layers, and $O_2$ gas accumulated at another electrode of said second solid electrolyte layer is released from a portion of the electrode exposed to the atmosphere at a side of the laminated body layers.

2. The measuring apparatus according to claim 1, further comprising means for sensing an oxygen concentration in the gas passed through said first electrolyte layer and for controlling said at least part of oxygen removed based on a sensed value.

3. The measuring apparatus according to claim 2, wherein said sensing means senses said oxygen concentration based on a voltage generated in a third solid electrolyte layer through which said gas passes, said third solid electrolyte layer being porous and being laminated between said first solid electrolyte layer and said second solid electrolyte layer.

4. The measuring apparatus according to claim 1, wherein at least some components contained in said gas are oxidized or deoxidized while passing through said first solid electrolyte layer by catalytic material mixed in said first solid electrolyte layer.

5. The measuring apparatus according to claim 1, wherein said second solid electrolyte layer is formed as a closely-compacted or dense body, and said apparatus is configured to heat said second solid electrolyte layer up to a temperature higher than a temperature of said first solid electrolyte layer.

6. A measuring apparatus for measuring $NO_X$ and HC components comprising:

a first porous solid electrolyte layer;

a second solid electrolyte layer;

gas-permeable electrodes provided at both sides of said first solid electrolyte layer and said second solid electrolyte layer;

first means for controlling current flowing through said first solid electrolyte layer and second means for controlling voltage across said second solid electrolyte layer, wherein at least said first solid electrolyte layer, said second solid electrolyte layer and said electrodes compose a laminated body on a heating device on which said second electrolyte layer is arranged nearer to the heating body than said first solid electrolyte layer, whereby $N_2$ gas or $CO_2$ gas accumulated at one of electrodes of said second solid electrolyte layer is released from a portion of the electrode exposed to the atmosphere at a side of the laminated body layers, and $O_2$ gas accumulated at another electrode of said second solid electrolyte layer is released from a portion of the electrode exposed to the atmosphere at a side of the laminated body layers, and a value based on the current flowing through said second solid electrolyte layer is output from the apparatus.

7. The measuring apparatus according to claim 6, wherein said electrodes comprise a first pair of gas-permeable electrodes provided at both sides of said first solid electrolyte layer and a second pair of gas-permeable electrodes provided at both sides of said second solid electrolyte layer, a porous insulating layer being disposed between said first solid electrolyte layer and said second solid electrolyte layer, and at least said first solid electrolyte layer, said first pair of gas-permeable electrodes, said second solid electrolyte layer, said second pair of gas-permeable electrodes and said insulating layer comprise said laminated body.

8. The measuring apparatus according to claim 6, further comprising:

a third solid electrolyte layer disposed between said first solid electrolyte layer and said second solid electrolyte layer, said third solid electrolyte layer being porous; and a pair of gas-permeable electrodes disposed at both sides of said third solid electrolyte layer, wherein said first control means performs control based on a voltage between said pair of electrodes disposed at both sides of said third porous solid electrolyte layer.

9. The measuring apparatus according to claim 6, wherein said laminated body is manufactured through a printing method.

10. The measuring apparatus according to clam 6, further comprising a catalyst in said laminated body to accelerate a chemical reaction of the component or components to be measured in a gas.

11. The measuring apparatus according to claim 6, wherein said laminated body does not have a vacant chamber, and wherein said electrodes comprise a first pair of gas-permeable electrodes provided at both sides of said first solid electrolyte layer and a second pair of gas-permeable electrodes provided at both sides of said second solid electrolyte layer, a porous insulating layer being disposed between said first solid electrolyte layer and said second solid electrolyte layer, and at least said first solid electrolyte layer, said first pair of gas-permeable electrodes, said second solid electrolyte layer, said second pair of gas-permeable electrodes and said insulating layer comprising said laminated body.

12. A combustion control apparatus comprising:

a combustion apparatus generating heat by combustion;

a catalyst disposed in an exhaust system of said combustion apparatus;

a gas component measuring apparatus according to any one of claim 1 and claim 6, said gas component measuring apparatus being disposed at a position downstream of said catalyst in said exhaust system; and a control means for controlling combustion in said combustion apparatus based on a measured value of a specified gas component measured by said gas component measuring apparatus.

* * * * *